United States Patent [19]
Loose

[11] Patent Number: 4,528,455
[45] Date of Patent: Jul. 9, 1985

[54] NON-DESTRUCTIVE TESTING SYSTEM WITH DUAL SCANNING

[75] Inventor: Timothy C. Loose, Chicago, Ill.

[73] Assignee: Magnaflux Corporation, Chicago, Ill.

[21] Appl. No.: 494,117

[22] Filed: May 13, 1983

[51] Int. Cl.[3] .......................................... G01N 21/88
[52] U.S. Cl. .................................. 250/563; 250/572; 358/106
[58] Field of Search ............. 250/562, 563, 572, 302, 250/303; 358/105, 106; 356/430, 431

[56] References Cited

U.S. PATENT DOCUMENTS 2,919,624  1/1960  Lindemann et al. ............... 250/563
3,777,169  12/1973  Walter et al. ...................... 358/106

Primary Examiner—David C. Nelms
Attorney, Agent, or Firm—Neuman, Williams, Anderson & Olson

[57] ABSTRACT

A system is disclosed in which a defect-indicating material is applied to the surface of a part which is scanned by a laser beam or by use of a television camera to develop electrical signals indicating defects. A comparison arrangement is provided for developing output signals only when signals are developed from the same portions of the scanned region during two scans, and a blower is provided for displacing extraneous elements between scans.

18 Claims, 10 Drawing Figures

NON-DESTRUCTIVE TESTING SYSTEM WITH DUAL SCANNING

This invention relates to a scanning type non-destructive testing system and more particularly to a system in which a region of a part is scanned to detect defect indications and in which adverse effects of extraneous elements are avoided in a manner such as to obtain highly accurate and reliable results. The system is comparatively simple and straightforward in operation and can be constructed and operated at reasonable costs. It is particularly suitable for automated operation, with minimal supervisory control.

BACKGROUND OF THE INVENTION

Scanning type non-destructive testing systems have heretofore been provided for detecting defect indications. For example, the O'Connor et al U.S. Pat. No. 3,744,030 and the Flaherty et al U.S. Pat. No. 3,774,162 disclose systems in which a laser beam is impinged on an oscillating mirror system to produce scanning movement over the surface of a part while light from the surface of the part is detected by photocell means to develop electrical signals indicating the position of defect-indicating material on the surface of the part. The defect-indicating material may be a penetrant material or it may include magnetic particles in dry form or in a liquid carrier, applied on the surface of a magnetizeable part during or after magnetization thereof. In either case, a fluorescent material may be associated with the defect-indicating material. As disclosed in the aforesaid O'Connor et al patent, the fluorescent material may be such as to respond to the wavelength of the laser beam to produce high energy emissions at a second wavelength and the detector may be arranged to have maximum sensitivity at the second wavelength. As a result, a high contrast is obtained, with high sensitivity and resolution.

Such prior systems have also included pattern recognition systems which are especially advantageous in certain applications such as, for example, in applications in which elongated cracks having a certain orientation are of primary interest.

With such systems, high satisfactory and reliable results have been obtained in many applications and the rejection of unsatisfactory parts has been insured with a very high degree of reliability. However, deficiencies of such systems have not been recognized. For example, it has not been appreciated that such systems may sometimes operate to indicate that a part should be rejected when, in fact, the part is satisfactory.

SUMMARY OF THE INVENTION

This invention was evolved with the general object of improving the accuracy and reliability of scanning type systems and of avoiding the unnecessary rejection of satisfactory parts while making certain that unsatisfactory parts are rejected.

The invention is based in part upon the discovery that in some testing operations, extraneous elements may produce the same indications as defects. For example, in the case of penetrant and magnetic particle inspection, particles of the penetrant material, particles of magnetic material or other particles may be in the path of a scanning beam or in the path between the surface of a part and a detector, to produce the same indication as an actual defect. Another important discovery is such extraneous elements can almost always be dislodged by effecting movement of the part or by effecting movement of the air or other fluid in which the part is being inspected and that by comparing the results of two tests, before and after effecting movement of the extraneous elements, it is possible to discriminate between elements which indicate an actual defect and extraneous elements which do not indicate an actual defect.

In accordance with the invention, means are provided for operating scanning means to sequentially perform first and second scans of a region of a part and electrical signals developed during such first and second scans are compared to develop output signals only when such electrical signals are developed from the same portions of the region during both the first and second scans. In addition, displacement means are provided for operating between the first and second scans to effect movement of extraneous elements relative to the part to preclude development of output signals therefrom.

With this arrangement, it is possible to obtain a high degree of accuracy and reliability as well as high sensitivity. The rejection of unsatisfactory parts can be assured while, at the same time, the rejection of satisfactory parts is avoided with a high degree of reliability.

The displacement means operates to disturb the relationship between the part and any extraneous elements and may comprise means for moving the part or means for repeating a magnetic particle, penetrant or other processing procedure between scans of the part. In one embodiment, the displacement means comprises a blower arranged to direct a stream of air between the scanning means and a surface region of the part.

The system is usable with a number of different types of scanning arrangements. In one embodiment, the part, such as a turbine blade, is scanned by a laser beam with a two-dimensional scan, a photo-multiplier or other type of detector being provided for detecting light transmitted from the part during the scanning with the laser beam.

In another embodiment, the entire region of the part to be scanned is illuminated and a detector such as a television camera tube is provided with a suitable optical system for detecting the light and for performing the scanning operation by scanning of the screen of the camera tube.

Additional important features of the invention relate to the manner in which the scanning operation is controlled and in which the signals developed during scanning are processed in order to obtain accurate and reliable operation. In one arrangement according to the invention, a complete two-dimensional scan is performed and all of the signals developed during the scan are stored. Then a second two-dimensional scan is performed and, again, all of the electrical signals developed are stored. Then both groups of stored signals are compared to determine those regions from which signals are obtained during both scans. Between the scanning of each portion of the scanned region and the subsequent scanning of the same portion, the movement of any extraneous elements may be effected, as by energizing a blower between the first and second scans. In the alternative, a blower may be continuously energized to produce movements of any extraneous elements between the two scans.

In another arrangement, the part is scanned and the electrical signals developed are stored. Then a second scan is performed in which each portion of the part is scanned, the electrical signal obtained, if any, is compared with the electrical signal, if any, stored from the previous scan and if signals have been developed during both scans, an output signal is then developed.

The output signal obtained in either type of system may be stored and a pattern recognition operation may be performed with respect thereto, if defects having a particular shape and orientation are of primary interest.

Also, with either type of system, a display may be provided for indicating the position and size of any indicated defects. Suitable audible alarms or visible indicating lights may be provided to signal the existence of a defect and signals are also developed for automatic control of apparatus to reject parts in an automated type of system.

This invention contemplates other objects, features and advantages which will become more fully apparent from the following detailed description taken in conjunction with the accompanying drawings which illustrate preferred embodiments of the invention.

DESCRIPTION OF PREFERRED EMBODIMENTS

Figure 1:
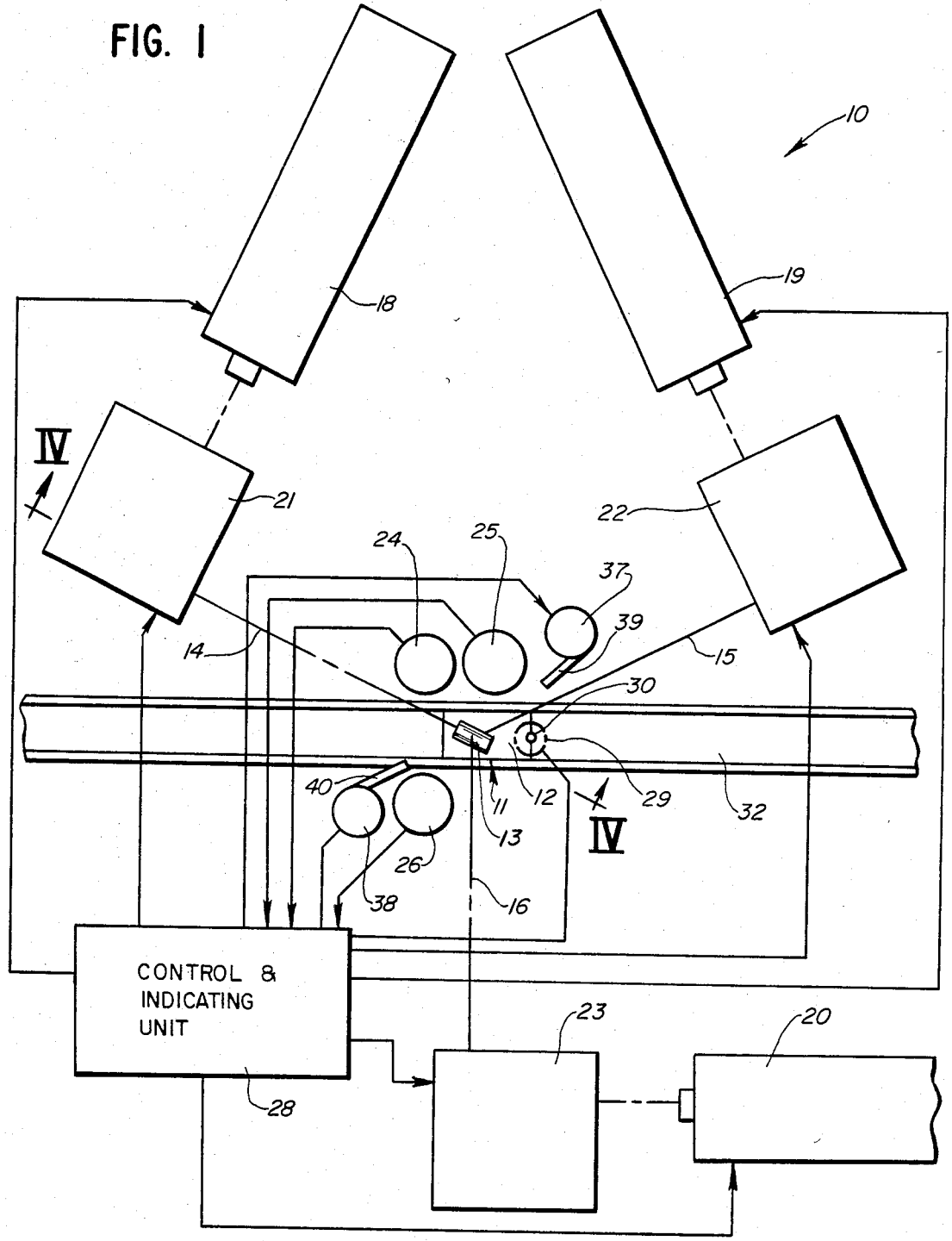
FIG. 1 is a plan view of scanning, detecting and indicating apparatus of the invention.

Reference numeral 10 generally designates scanning, detecting and indicating apparatus of a testing system constructed in accordance with the principles of the invention. The apparatus 10 as illustrated is designed for use in the detection of defects such as cracks in turbine blades. It operates by optical detection of an indicating material which is positioned on the surface of a blade over a defect therein, after processing of the blade.

As shown, a turbine blade 11 is supported on a mounting block 12 which is temporarily held at an inspection position for scanning by three laser beams from three different angles. The blade 11 is supported at its free end to permit inspection of regions of the blade which is adjacent a mounting base portion 13 thereof and at which a serious defect is most likely to occur.

The three laser beams are indicated by broken lines 14, 15 and 16 and are produced from three laser units 18, 19 and 20 by three scanning units 21, 22 and 23, each of which includes oscillating mirrors for producing two-dimensional scans. Three detectors 24, 25 and 26 are provided, each of which may include a photomultiplier tube, for detection of light from the scanned surface regions of the blade 11.

A control and indicating unit 28 is connected to the laser units 18–20 and to the scanning units 21–23 and the detectors 24–26. The unit 28 is also connected to a solenoid 29 which, as diagrammatically illustrated, is connected to a pin in the path of the block 12. The pin 30 operates to temporarily hold the block 12 and the blade 11 thereon against movement by a conveyor 32 during the optical inspection of the blade 11. The solenoid 29 may be physically mounted below the conveyor and the pin 30 may be directly connected to the armature thereof.

The illustrated conveyor 32 is of a type having bristles inclined upwardly and forwardly to support the block 12, the bristles being oscillated at a rapid rate between forward and rearward directions to advance the block 12 when not held by the holding pin 30.

Figure 2:
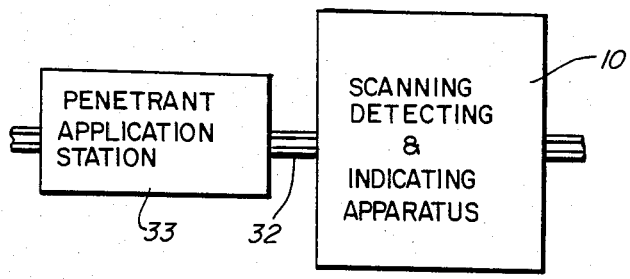
FIG. 2 diagrammatically illustrates penetrant equipment for processing parts before movement to the apparatus of FIG. 1.

As shown in FIG. 2, the conveyor 32 may receive the block 12 and the blade thereon from a penetrant applicator station 33 at which a liquid penetrant material is applied to the blade 11. Suitable penetrant materials are available which will penetrate otherwise invisible cracks, porosity, seams and other defects open to the surface and to make such defects readily visible and also readily detectable by optical means.

Figure 3:
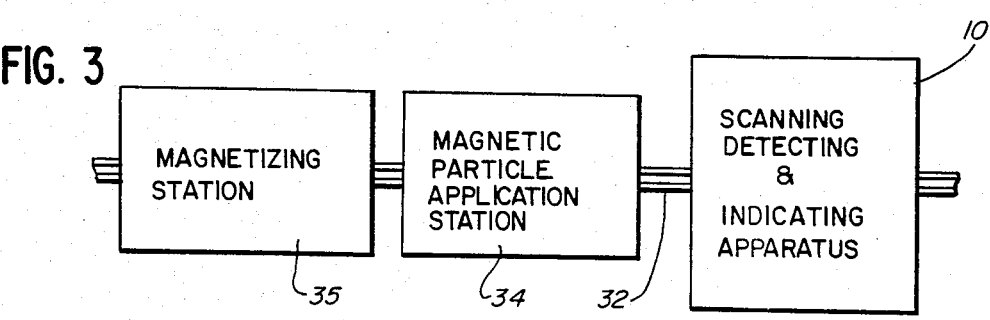
FIG. 3 diagrammatically illustrates magnetic particle equipment for processing parts before movement to the apparatus of FIG. 1.

Alternatively, as shown in FIG. 3, the conveyor 32 may receive the block 12 and the blade 11 thereon from a magnetic particle applicator station 34 which may receive the blades from a magnetizing station 35. At the magnetic particle applicator station 34, ferro-magnetic particles are applied to the surface of the blades, such magnetic particles being applied by hand or automatically, and either as dry powder or in a fluid or liquid suspension, as by using a water or oil suspension. When such particles are applied, during or after magnetization of a part, they concentrate over leakage fields produced where there are cracks or discontinuities in the part.

As aforementioned, it is found that extraneous elements may be in the path of the scanning laser beams 14–16 to produce false indications of defects. Typically, such extraneous elements may be magnetic particles or they may be particles or droplets of a penetrant material. Dust particles may also act as the extraneous elements. In accordance with this invention, displacement means are provided for effecting movement of such extraneous elements and in the system 10, a pair of blowers 37 and 38 are provided which supply air to nozzles 39 and 40 for impinging streams of air on the opposite sides of the blade 11.

Figure 4:
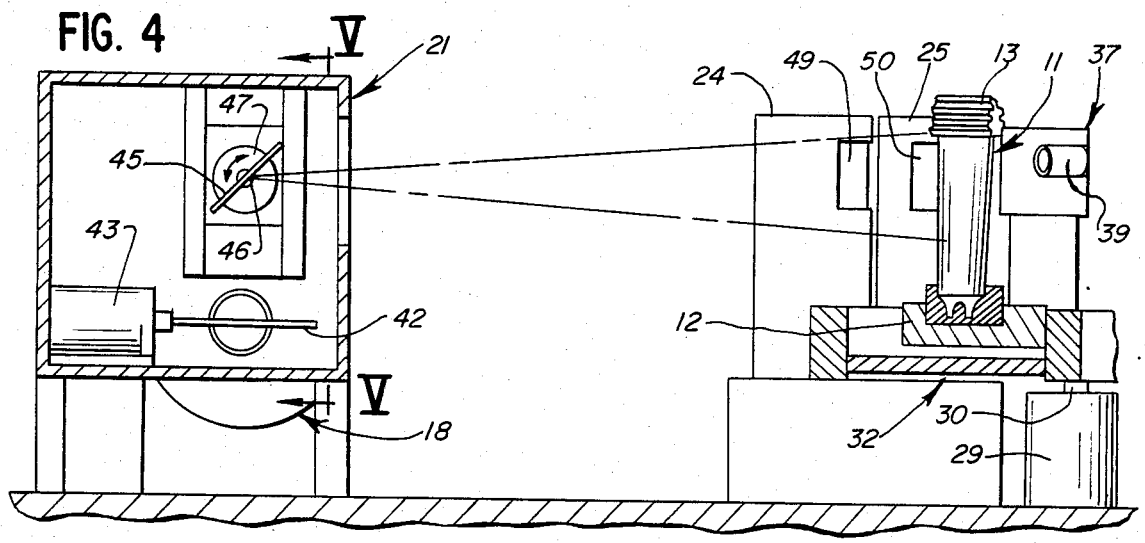
FIG. 4 is a sectional view on an enlarged scale, taken substantially along line IV—IV of FIG. 1 and illustrating the construction of a scanning unit.
Figure 5:
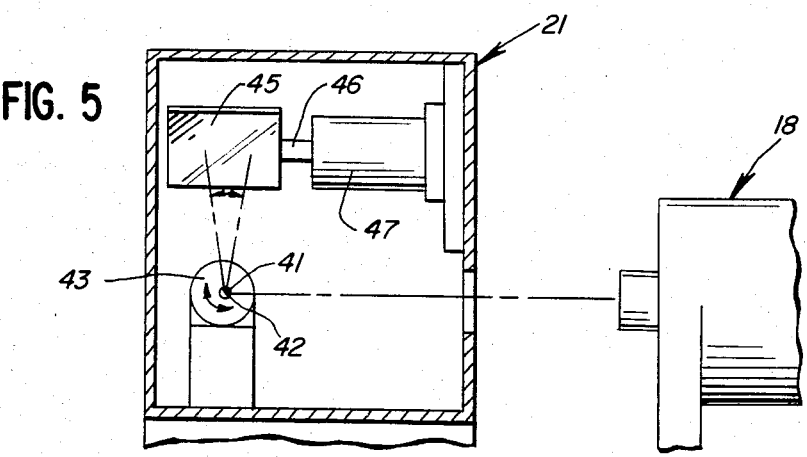
FIG. 5 is a sectional view taken substantially along line V—V of FIG. 4.

FIGS. 4 and 5 illustrate the construction of the scanning unit 21 and FIG. 4 also illustrates the relationship of the turbine blade 11 with respect to the detector units and the conveyor structure. The scanning unit 21 comprises a first mirror 41 on an oscillatory shaft 42 of a motor 43. The mirror 41 is in the path of the beam from the laser 18 and operates to direct the beam upwardly to a second mirror 45 which is carried by an oscillatory shaft 46 of a second motor 47. The beam is reflected from the mirror 45 to the blade 11 and it will be appreciated that by controlling the oscillatory movements of the mirrors 41 and 45, a raster scan is developed.

The detectors 24 and 25 as illustrated are photomultiplier tubes having windows 49 and 50 positioned to detect light reflected from the blade 11 when it is scanned by the laser beams 14 and 15. It will be understood that the detector 26 is of similar construction. Each of the detectors may include a suitable filter for responding primarily to the wavelength of the laser or, when a fluorescent material is used, to the wavelength of light developed by the fluorescent material when it is impinged by the laser beam.

It is noted that the three scanning systems and detectors are used in order to thoroughly scan regions of the turbine blade 11 at which serious defects are most likely to occur. In general, such defects are in proximity to the mounting base portion 13 and may also be in the leading edge of the blade, it being noted that the laser beam 14 and detector 24 are used for scanning the leading edge of the blade 11.

It should also be noted that although the system of the invention is particularly advantageous in detecting defects in turbine blades, various features of the invention are not limited to the testing of turbine blades and may be used in other applications.

Figure 6:
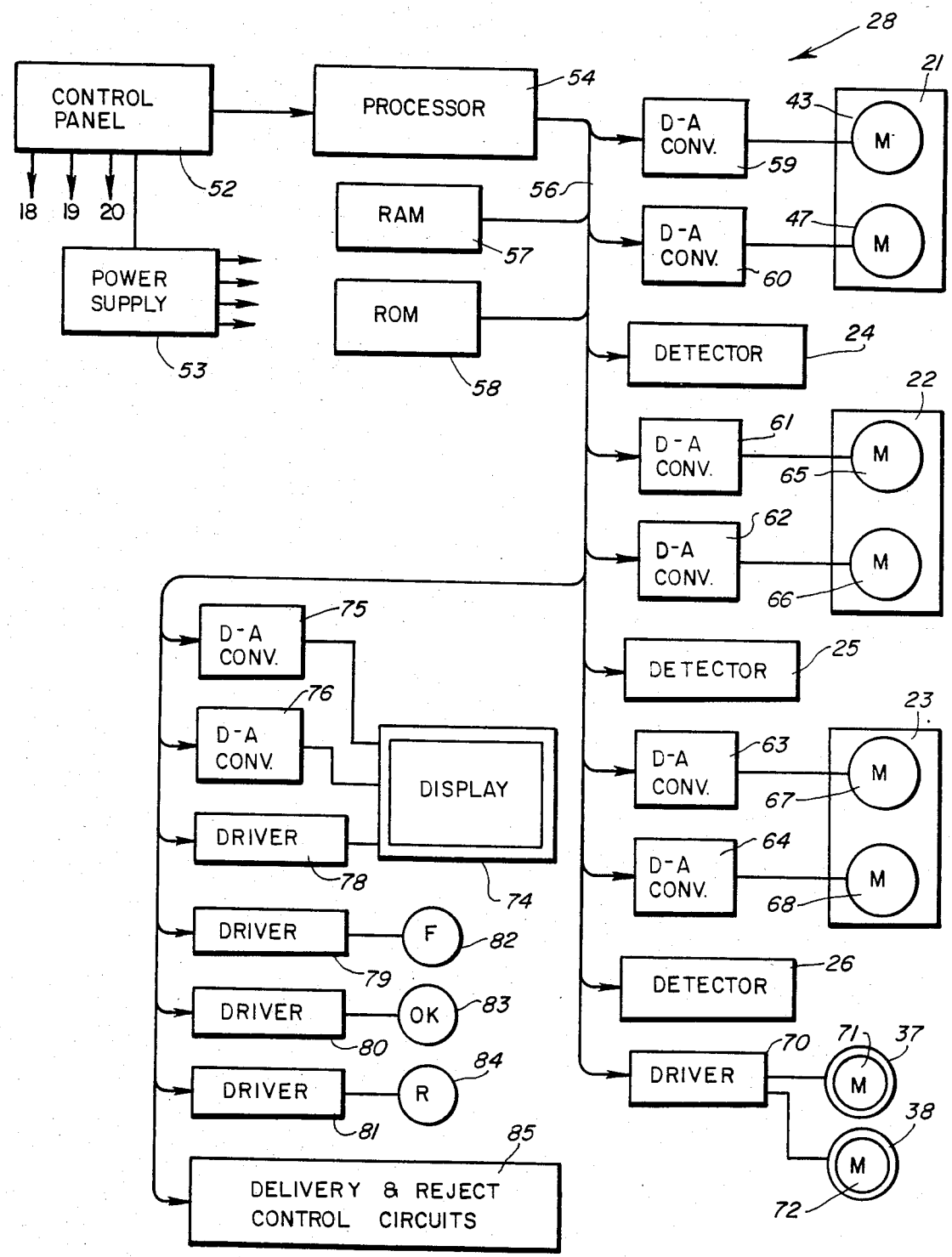
FIG. 6 illustrates circuitry of a control and indicating unit of the apparatus of FIG. 1.

FIG. 6 illustrates circuitry of the control and indicating unit 28. The unit 28 includes a control panel 52 which is connected to the laser units 18, 19 and 20 and which is connected to a power supply 53 for supplying power to a processor 54 and to other circuits of the unit 28. The processor 54 is connected to a data bus 56 which is connected to a random access memory 57 and to a read only memory 58. The bus 56 is also connected to the photomultiplier detector tubes 24, 25 and 26 and to various other circuits including three pairs of digital-to-analog converter circuits 59 and 60, 61 and 62, and 63 and 64. The converters 59 and 60 supply control signals to the motors 43 and 47 to oscillate the mirrors 41 and 45 of the scanning unit 21. Similarly, converters 61 and 62 are connected to motors 65 and 66 of the scanning unit 22 and converters 63 and 64 are connected to motors 67 and 68 of the scanning unit 23.

A driver 70 is provided for controlling energization of drive motors 71 and 72 for the blowers 37 and 38.

The unit 28 further includes a display 74 which may include a cathode ray tube and which may include horizontal and vertical deflection circuits controlled from the outputs of digital-to-analog converters 75 and 76. An intensity control input of the display 74 is connected to the output of a driver 78.

As also illustrated, drivers 79, 80 and 81 are provided for controlling energization of a "Flaw" signal light 82, a "Part OK" signal lamp 83 and a "Reject" signal lamp 84. In addition, delivery and reject control circuits 85 may be connected to the bus 56 for operation from the processor 54 to control the delivery of a blade to the test position, to control operation of the solenoid 29 to release a blade from the test position and to control rejection at a down-line position of a blade found to be defective.

Figure 7:
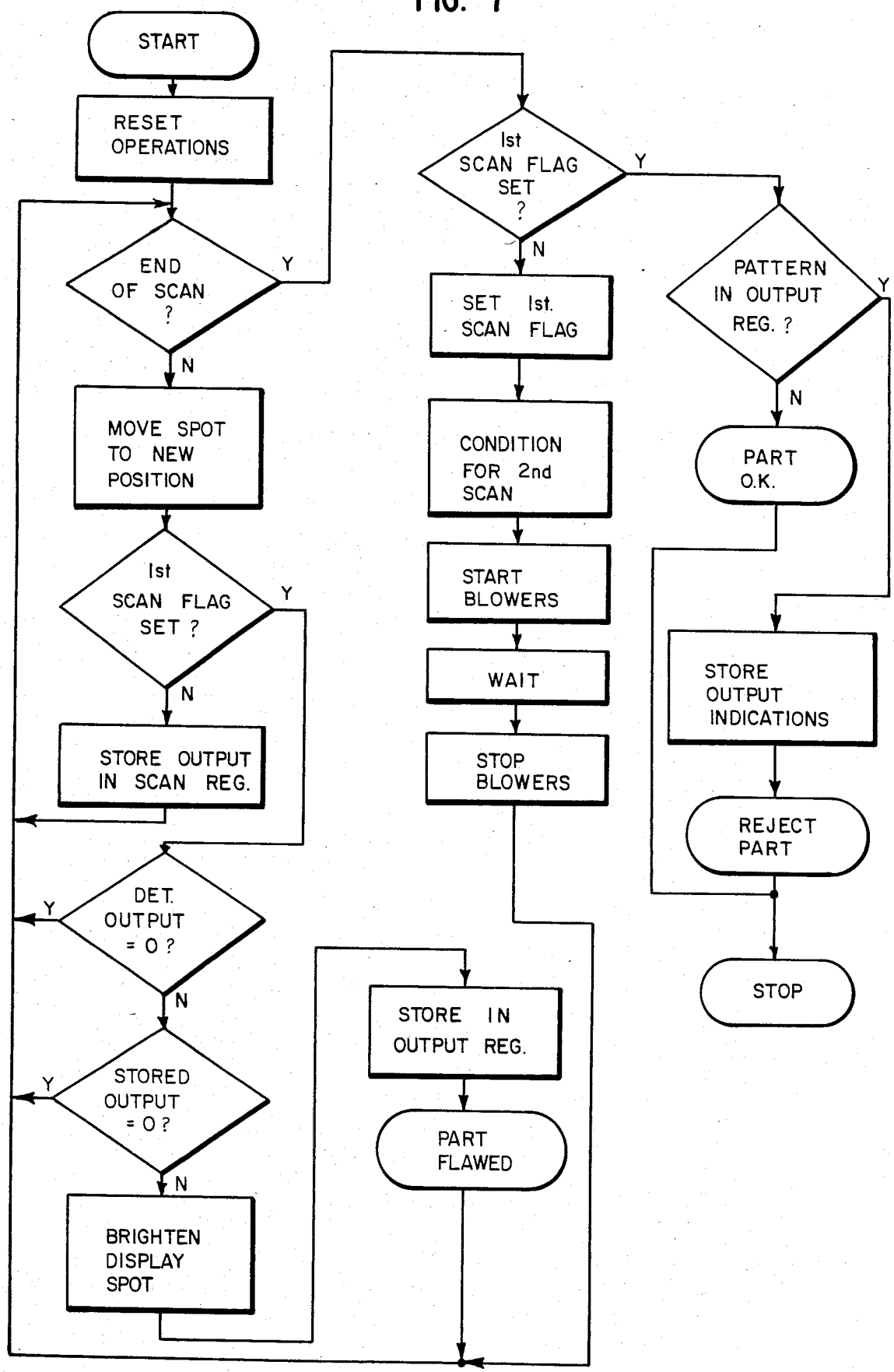
FIG. 7 is a flow chart illustrating one mode of operation of the circuitry of FIG. 6.

FIG. 7 is a flow chart illustrating one mode of operation. First, reset operations are performed to place flags and memories in predetermined initial conditions. Then an end of scan test is performed and if the scanning circuits are not at a final or end position, a scanning spot is moved to a new position. This may be accomplished, for example, through rotation of one of the scanning mirrors through a small angle and through rotation of the other scanning mirror through a much smaller angle, a raster type scan being obtained. If a first scan flag is not set, indicating that the scan being performed is the first scan of the area in question, the output from the photomultiplier detector is stored in a scan register at a position corresponding to the position of the scanning spot. This operation is then repeated until an end of scan signal is detected. Then a test is performed to determine whether the first scan flag is set. If not, it is set and the system is conditioned for a second scan operation. Also, the blower motors 71 and 72 are energized, a delay operation is performed and the blower motors are then deenergized.

Energization and deenergization of the blowers between scans is an optional feature. In many cases, the blowers may be operated continuously and so long as there is a delay between one scan and the next, the desired movement of extraneous elements may be effected. In other cases, however, it may be desirable to momentarily energize the blowers, or to apply a jarring force to the part under test or to repeat a magnetic particle, penetrant or other processing procedure or otherwise effect movement of the extraneous particles.

After conditioning for the second scan, the scanning spot is moved again from one position to another. The second scan differs from the first scan in that the output of the photomultiplier detector is not stored in the scan register. Instead, a test is performed periodically in timed relation to the scanning movement to determine whether the detector output is zero. If it is not zero, another test is made to determine whether the stored output at the corresponding position is zero. If neither is zero, the spot on the display 74 is brightened, it being noted that the horizontal and vertical deflection circuits of the display may be operated in synchronism with the scanning operation. In addition to brightening the display, a signal is stored in an output register and the flaw signal lamp 82 may be energized.

At the end of the second scan, a pattern will be stored in the output register corresponding to elements from which signals have been obtained during both scans. Extraneous elements which have been moved between the first and second scans will produce no signals such as to be stored in the output register and, as a result, a very high degree of discrimination is obtained with respect to eliminating the effects of extraneous elements.

In certain applications and especially in the case of turbine blades, any signal detected in both scans may be sufficiently serious to warrant rejection of the part. In other applications, it may be desirable to reject the part only when predetermined patterns of indications are obtained. For example, it may be desirable to respond only to cracks having a predetermined orientation in a part. In such cases, a test is made to determine whether a predetermined pattern exists in the output register. For example, the arrangement as disclosed in the Flaherty et al U.S. Pat. No. 3,774,162 may be used. If no pattern is detected, the "Part OK" lamp 83 may be energized but if the pattern is detected, the information stored in the output register may be permanently recorded for future recall and analysis and the "Reject" lamp 84 may be energized.

Figure 8:
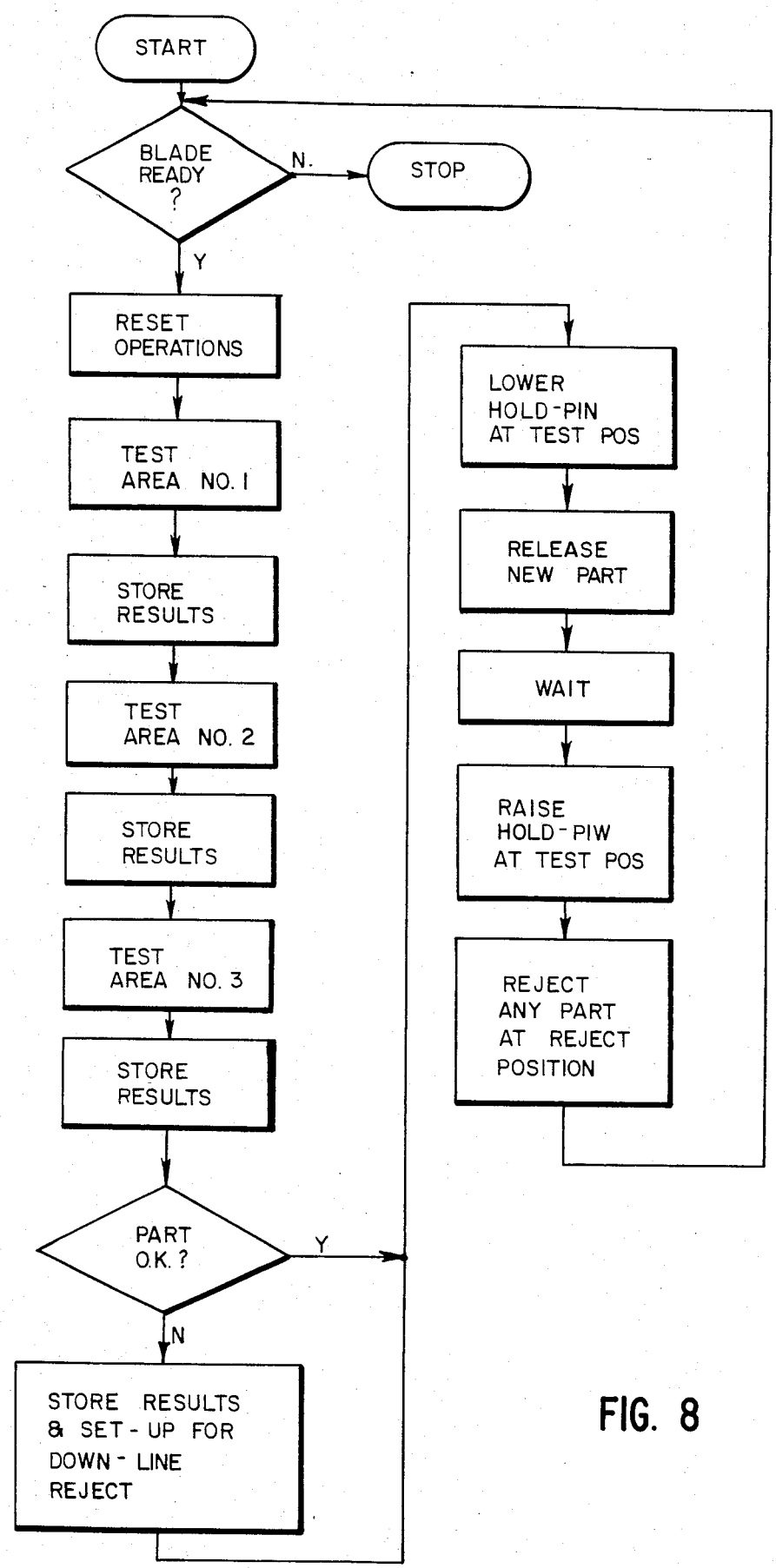
FIG. 8 is a flow chart illustrating another mode of operation of the circuitry of FIG. 6.

FIG. 8 is a flow chart illustrating an operation involving sequential use of the three laser beams 14, 15 and 16, it being noted that the flow chart of FIG. 7 illustrates an operation using only one of the laser beams and the associated scanning unit and detector to scan one area of a part. In the operation depicted in FIG. 8, a test is made to determine whether a blade is ready at a test position such as illustrated in FIG. 1 and if so, reset operations are performed and then three tests are made sequentially with the laser beams 14–16, the results of each test being stored. In each case, an operation is performed as illustrated in FIG. 7. The output indications are stored in three separate registers or memory locations.

If a predetermined indication or pattern is stored from any one of the three test operations, indicating that the part is not OK, the results are stored for future reference and examination and the system is set up for a down-line rejection of the part. For example, a pin similar to the pin 30 may be elevated at a down-line position in the conveyor 32. Then a series of operations are performed which are the same whether or not the part is OK.

First, the holding pin 30 is lowered at the test position and at about the same time, a part may be released from a processing station such as the penetrant applicator station 33 or the magnetic particle applicator station 34, illustrated in FIGS. 2 and 3. The part may be released by lowering a holding pin at the processing station.

Then after waiting for a time interval sufficient for the block 12 to move past the location of the pin 30, the pin 30 is raised to its initial position to receive the block moving down-line from the processor station.

Finally, any part being held at the down-line reject position may be moved off the conveyor 32, as by pushing it to one side. The operation may then be repeated and in this way, the blades may be processed and inspected automatically.

Figure 9:
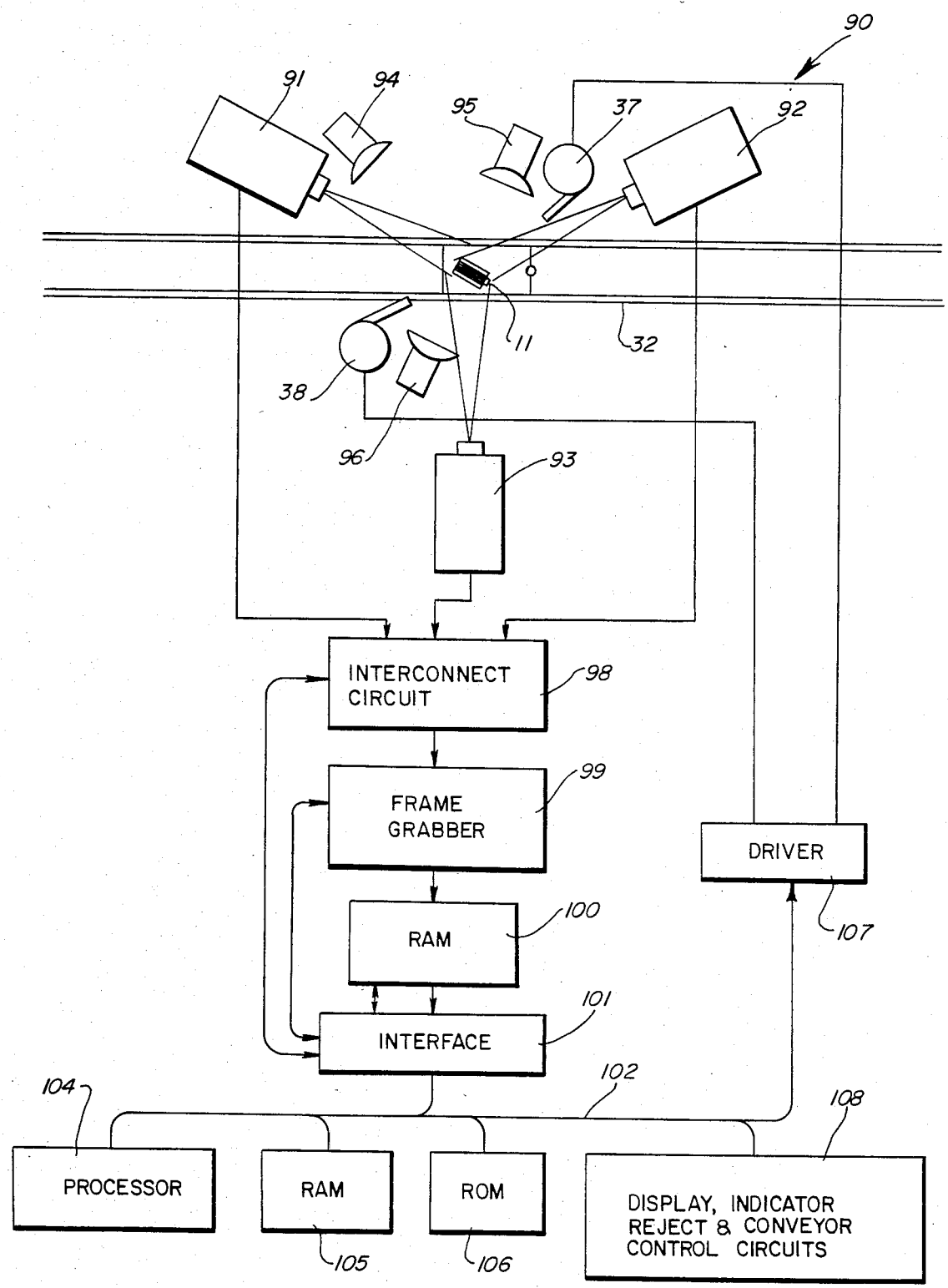
FIG. 9 illustrates diagrammatically another form of scanning, detecting and indicating apparatus according to the invention.

FIG. 9 illustrates diagrammatically another form of scanning, detecting and indicating apparatus constructed in accordance with the invention, generally designated by reference numeral 90. In the apparatus 90, three television cameras 91, 92 and 93 are used in place of the laser scan systems of the system 10, three light sources 94, 95 and 96 being provided for illuminating the blade 11. Cameras 91, 92 and 93 are connected through an interconnect circuit 98 to a frame grabber 99 which is connected to a random access memory 100. The interconnect circuit 98, frame grabber 99 and memory 100 are controlled through an interface circuit 101 from a bus 102 which is connected to a processor 104, a random access memory 105 and a read-only memory 106. Bus 102 is also connected through a driver 107 to motors of the blowers 37 and 38 and it is also connected to display, indicator, reject and conveyor control circuits as indicated by the block 108, similar to those illustrated in FIG. 6.

Figure 10:
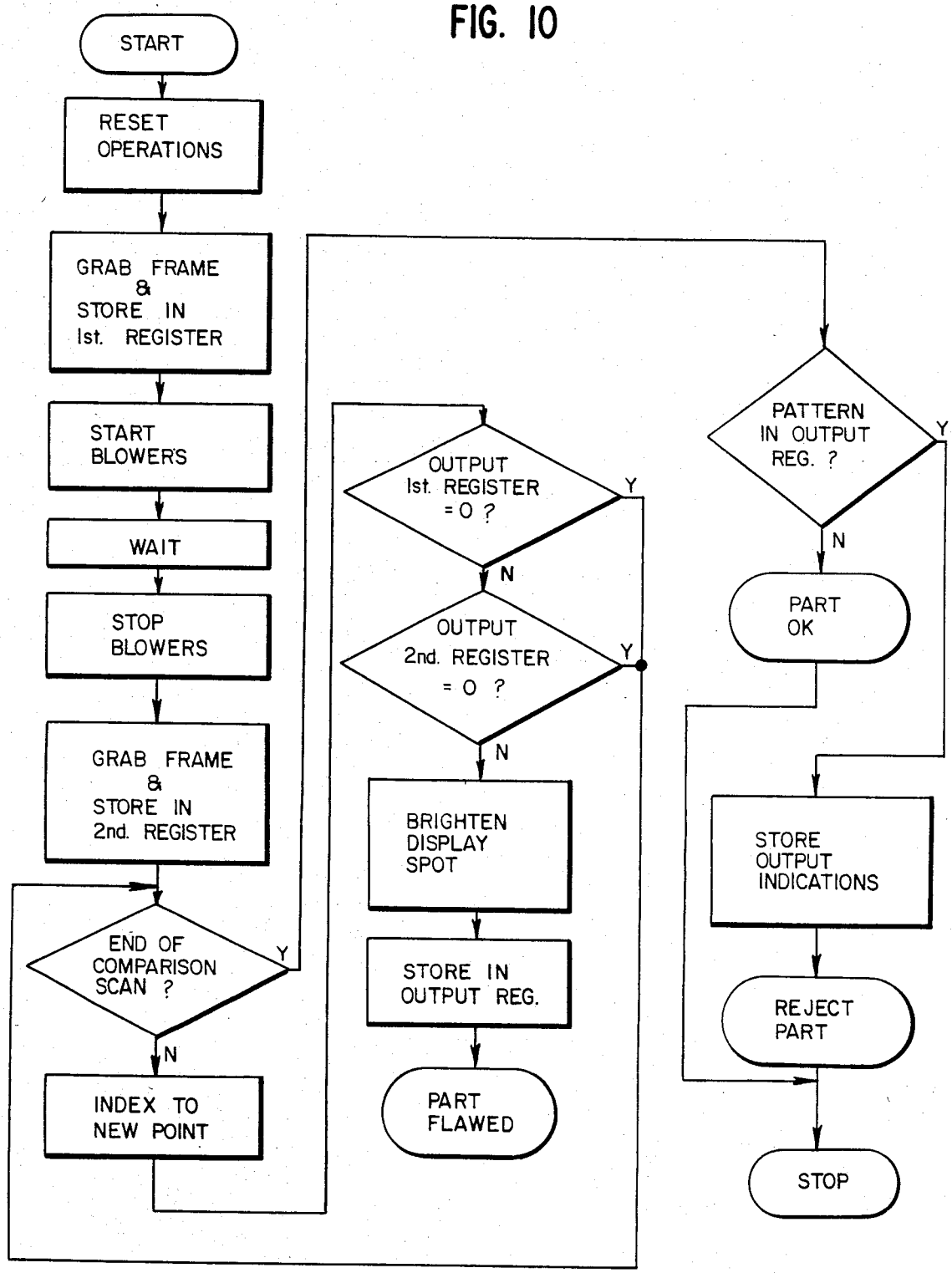
FIG. 10 is a flow chart illustrating a mode of operation of the apparatus of FIG. 9.

FIG. 10 is a flow chart illustrating the operation of the apparatus 90 of FIG. 9. The operation as depicted involves the use of only one of the cameras 91–93, but it will be understood that three cameras may be used, with an operation similar to that depicted in FIG. 8.

In the operation as shown in FIG. 10, reset operations are performed and then the frame grabber 99 is operated to store signals from one scan of an area of the part in one section of the memory 100. Then after energizing, waiting and de-energizing motors of the blowers 37 and 38, the frame grabber 99 is again operated and signals developed during a second scan are stored in a second portion of the memory 100.

Then a comparison operation is performed, the two portions of the memory 100 being compared. After determining that the comparison scan has not been completed, scan control registers are indexed. If the signal stored at either of the two corresponding points of the memory portions is zero, the index operation is repeated. If not, i.e., if signals are stored at both corresponding points, the display may be brightened and a signal is stored in an output register. Then a flaw signal lamp may be energized, the operation being repeated until the comparison scan is completed.

Next, the output register may be scanned for a predetermined pattern. If no defect-indicating pattern is found, a "Part OK" signal lamp is energized. However, if a defect-indicating pattern is found, the part may be marked, the signals in the output register may be stored for future reference and examination and the part may be rejected.

It will be understood that modifications and variations may be effected. As above noted, the blower operation may be effected only between scans or it may be effected continuously. It is also possible to use means other than a blower for effecting movement of extraneous elements between scans. For example, a sharp impact may be applied to the part between scans or a vibratory force may be applied to the part, either between scans or continuously, sufficient to effect movement of extraneous elements without disturbing the position of defect-indicating elements.

It will be understood that other modifications and variations may be effected without departing from the spirit and scope of the novel concepts of this invention.

I claim as my invention:

1. In a system for non-destructive testing of a part to indicate defects therein, scanning means operative to scan a region of the part and to develop electrical signals in response to both defects which are in stationary relation to the part and extraneous elements which are movable relative to the part, means for operating said scanning means to sequentially perform first and second scans of said region, comparison means for comparing electrical signals developed during said first and second scans to develop output signals only when electrical signals are developed from the same portions of said region during both of said first and second scans, and displacement means operative between said first and second scans to effect movement of said extraneous elements relative to said part to preclude development of output signals therefrom.

2. In a system as defined in claim 1, said scanning means being operative through propagation of energy to impinge on the part, the amplitude of the signal developed from each small portion of said region during a scanning operation being a function of the existence of a defect therein and also being a function of the energy propagation characteristics of a narrow path, said displacement means being operative to move particle elements out of said path between said first and second scans.

3. In a system as defined in claim 1, said displacement means being electrically energizeable.

4. In a system as defined in claim 3, means for energizing and then deenergizing said displacement means between said first and second scans.

5. In a system as defined in claim 2, said scanned region being a surface region of said part, said displacement means comprising blower means arranged to direct a stream of air between said scanning means and said surface region of said part.

6. In a system as defined in claim 2, said scanning means comprising an energy source, means for propagating energy in a narrow beam from said source toward said part, means for effecting movement of said beam relative to said part, and detector means for detecting energy propagated from said scanned region.

7. In a system as defined in claim 6, said energy source being a light source.

8. In a system as defined in claim 7, said energy source being a laser.

9. In a system as defined in claim 2, said scanning means comprising an energy source, means for propagating energy from said energy source toward said scanned region, detector means in spaced relation to said scanned region for operating at each instant of time to respond only to energy propagated from a small spot portion of said scanned region, and means associated with said detector means for effecting scanning movement of said spot portion relative to said part.

10. In a system as defined in claim 9, said detector means comprising a television camera.

11. In a system as defined in claim 1, wherein said scanning means is operative to scan a surface region of the part and wherein extraneous elements of particulate form may lightly adhere to said surface region, said displacement means being operative to displace said particles along said surface between said first and second scans.

12. In a system as defined in claim 1, said comparison means comprising memory means for storing signals developed during said first scan, and means operative during said second scan for comparing signals developed during said second scan with signals stored from said first scan to develop said output signals.

13. In a system as defined in claim 1, said comparison means comprising memory means for storing signals developed during said first and second scans, and means operative after said second scan for scanning said memory means to develop said output signals.

14. In a system as defined in claim 1, memory means for storing said output signals, and means for scanning said memory means to develop a control signal only in response to storage of output signals in a predetermined pattern.

15. In a system as defined in claim 1, said scanning means being operative to repetitively scan said region at a certain frame rate, and said comparison means including frame grabber means and memory means operated in conjunction with said frame grabber means to store signals in said first scan and subsequently in said second scan.

16. In a system as defined in claim 1, means operative before operation of said scanning means to apply a defect-indicating material to a surface of said part to form said region scanned by said scanning means.

17. In a system as defined in claim 16, said defect-indicating material being a penetrant material.

18. In a system as defined in claim 16, said defect-indicating material including magnetic particles applied on the surface of the part during or after magnetization thereof.

* * * * *